United States Patent [19]

Leng et al.

[11] Patent Number: 5,593,663
[45] Date of Patent: Jan. 14, 1997

[54] ANTIPERSPIRANT MATERIALS AND COMPOSITIONS

[75] Inventors: Francis J. Leng, Gayton; David T. Parrott, Birkenhead, both of United Kingdom

[73] Assignee: Chesebrough-Pond's USA Co., Division of Conopco, Inc., Greenwich, Conn.

[21] Appl. No.: 339,378

[22] Filed: Nov. 14, 1994

Related U.S. Application Data

[63] Continuation of Ser. No. 975,309, Nov. 12, 1992, abandoned.

[30] Foreign Application Priority Data

Nov. 12, 1991 [GB] United Kingdom ............... 9123978
Nov. 12, 1991 [GB] United Kingdom ............... 9123979

[51] Int. Cl.$^6$ ............................................. A61K 7/32
[52] U.S. Cl. ................................................. 424/65
[58] Field of Search ..................................... 424/65

[56] References Cited

U.S. PATENT DOCUMENTS

| | | | |
|---|---|---|---|
| 3,326,768 | 6/1967 | MacMillan | 424/68 |
| 3,678,156 | 7/1972 | MacMillan et al. | 424/68 |
| 3,767,786 | 10/1973 | MacMillan | 424/68 |
| 3,852,431 | 12/1974 | Motov et al. | 424/68 |
| 3,959,459 | 5/1976 | Curry | 424/68 |
| 4,137,306 | 1/1979 | Rubino et al. | 424/68 |
| 4,219,540 | 8/1980 | Soldati et al. | 424/68 |
| 4,229,432 | 10/1980 | Geria | 424/68 |
| 4,508,705 | 4/1985 | Chandhuri et al. | 424/68 |
| 4,526,780 | 7/1985 | Marschner et al. | 424/68 |
| 4,605,554 | 8/1986 | Prussin et al. | 424/68 |
| 4,724,139 | 2/1988 | Palinczar | 424/68 |
| 4,749,569 | 6/1988 | Gianino et al. | 424/68 |
| 4,921,694 | 5/1990 | Hoppe et al. | 424/65 |
| 4,999,348 | 3/1991 | Cioca et al. | 514/171 |
| 5,143,718 | 9/1992 | Bar-Shalom | 424/47 |

FOREIGN PATENT DOCUMENTS

| | | | |
|---|---|---|---|
| 0103911 | 3/1984 | European Pat. Off. | 424/68 |
| 0103910 | 3/1984 | European Pat. Off. | 514/847 |
| 0224457 | 6/1987 | European Pat. Off. | 424/401 |
| 0253552 | 1/1988 | European Pat. Off. | 424/68 |
| 0279328 | 8/1988 | European Pat. Off. | 424/68 |
| 0291334 | 11/1988 | European Pat. Off. | 424/68 |
| 0366230 | 5/1990 | European Pat. Off. | 424/68 |
| 0433132 | 6/1991 | European Pat. Off. | 424/68 |
| 0466236 | 1/1992 | European Pat. Off. | 424/66 |

(List continued on next page.)

OTHER PUBLICATIONS

Kabara, Jon J. et al., "Antimicrobial Action of Isomeric Fatty Acids on Group A Streptoccous", Journal of Medicinal Chemistry, vol. 16, No. 9 (1973) pp. 1060–1062.

Conley, Anthony J. et al., "Antimicrobial Action of Esters of Polyhydric Alcohols", Antimicrobial Agents and Chemothrapy, Nov. 1973, vol. 4, No. 5, pp. 501–506.

Beuchat, L. R., "Comparison of Anti–vibrio Activities of Potassium sorbate, Sodium Benzoate and Glycerol and Sucrose Esters of Fatty Acids", Applied and Environmental Microbiology, vol. 39, No. 6 (Jun. 1980), pp. 1178–1182.

(List continued on next page.)

*Primary Examiner*—Shelley A. Dodson
*Attorney, Agent, or Firm*—Rimma Mitelman

[57] ABSTRACT

Novel antiperspirant actives are amphiphilic materials which form, upon contact with perspiration, a water-insoluble liquid crystal phase of greater than one-dimensional periodicity, e.g. a cubic (three-dimensional periodicity) or hexagonal (two-dimensional periodicity) liquid crystal structure. Examples of such actives include lipids, surfactants, emulsifiers, polymer amphiphilic complexes and block copolymer surfactants which form the required liquid crystal phase upon contact with sweat. Preferably, antiperspirant compositions comprising the novel active(s) are free of conventional antiperspirant actives, especially aluminum and/or zirconium salts.

5 Claims, 5 Drawing Sheets

FOREIGN PATENT DOCUMENTS

| | | | |
|---|---|---|---|
| 2274277 | 1/1976 | France | 424/68 |
| 59-33206 | 2/1984 | Japan | 424/68 |
| 60-87206 | 5/1985 | Japan | 424/68 |
| 967591 | 8/1964 | United Kingdom | 424/68 |
| 735681 | 8/1966 | United Kingdom | 424/68 |
| 1439244 | 6/1976 | United Kingdom | 424/68 |
| 2009617 | 6/1979 | United Kingdom | 424/68 |
| 2050162 | 1/1981 | United Kingdom | 424/68 |
| 2091099 | 7/1982 | United Kingdom | 424/68 |
| 84/02076 | 6/1974 | WIPO | 424/401 |
| 92/04885 | 4/1992 | WIPO | 424/68 |

OTHER PUBLICATIONS

"Final Report on the Safety Assessment of Glyceryl Oleate", Journal of the American College of Toxicology, vol. 5, No. 5, (1986), pp. 391–413.

Bahadur, P., et al. "Block Copolymers—A Special Class of Surfactants", Tenside Surf. Det. 28 (1991) 3, pp. 1713–179.

Krog, Food Emulsifiers, pp. 147–165.

Ericsson, "Lipid–Protein Interactions", pp. 193–199. (1970).

Fontell, K., "X-ray Diffraction by Liquid Crystals—Amphiphilic Systems", Liquid Crystals and Plastic Crystals, vol. 2, (1974), pp. 80–109.

Luzzati, V., "X-ray Diffraction Studies of Lipid–Water Systems", Biological Membranes, (1968), pp. 71–123.

Reller, H. H. et al. "Effects of Topically Applied Agents on the Eccrine Sweat Glands", pp. 2–10. (1968).

European Search Report. Feb. 22, 1993.

Abstract of JP 54035215 Mar. 15, 1979.

Fontell, Krster, "Liquid Crystalline Behavior in Lipid–Water Systems", Prog. Chem. Fats Other Lipids, vol. 16, (1978) pp. 145–162.

Abstract of FR 2,274,277. Jan. 9, 1976.

Abstract of EP 0 433 132. Dec. 13, 1989.

(w/w %)

(w/w %)

(w/w %)

5,593,663

ANTIPERSPIRANT MATERIALS AND COMPOSITIONS

This is a continuation of application Ser. No. 07/975,309, filed Nov. 12, 1992, now abandoned.

FIELD OF THE INVENTION

The invention relates to antiperspirant actives, and antiperspirant compositions suitable for topical application to the human skin, in any product form. These can be, for example, as liquid compositions suitable for use in a roll-on dispenser, solid compositions for use as a cosmetic stick together with a stick holder, a liquid composition suitable for dispensing from a propellant-driven aerosol container or a pump spray, or a cream suitable for dispensing from a suitable container or for manual delivery using the fingers. The invention also relates to the novel use of certain materials as antiperspirant actives.

BACKGROUND OF THE INVENTION

The antiperspirant market and the technical and patent literature in the field of antiperspirants are dominated by products based on metal salts, for example aluminium or zirconium salts such as aluminium chloride, aluminium chlorohydrate, zirconium hydroxychloride, to name but a few, which are intended to reduce or prevent perspiration at the skin surface, particularly on the underarm.

However, doubts as to the safety in use of aluminium salts have stimulated research for alternative antiperspirant actives.

We have surprisingly found that a class of compounds, hitherto unconsidered for their effect as antiperspirant actives, in fact can exhibit remarkably good performance as antiperspirant actives, and are even compatible with known antiperspirant type formulations.

SUMMARY OF THE INVENTION

Accordingly, in a first aspect the present invention provides an antiperspirant composition suitable for topical application to the human skin, comprising an antiperspirant active which comprises at least one amphiphilic material, the antiperspirant active being one which forms, upon contact with perspiration, a water-insoluble liquid crystal phase of greater than one-dimensional periodicity.

It is to be understood in the context of the invention that "amphiphilic material" may include a mixture of materials, at least one of which is amphiphilic.

In a second aspect the invention provides a method of preventing or reducing perspiration at the human skin surface, comprising applying thereto an antiperspirant composition comprising an antiperspirant active which comprises at least one amphiphilic material, the antiperspirant active being one which forms, upon contact with perspiration, a water-insoluble liquid crystal phase of greater than one-dimensional periodicity.

According to preferred embodiments of the above aspects of the invention, the antiperspirant composition is free or substantially free of antiperspirant or deodorant levels of metal salts, especially those metal salts used in the prior art as antiperspirant or deodorant actives.

In a third aspect the invention provides the novel use as an antiperspirant active of an amphiphilic material, which active forms, upon contact with perspiration, a water-insoluble liquid crystal phase of greater than one-dimensional periodicity.

The present invention, in particular the various aspects and preferred embodiments thereof, will now be described in detail further below and in the Examples which follow with reference to the accompanying drawings.

DESCRIPTION OF PREFERRED EMBODIMENTS

Figure 1:
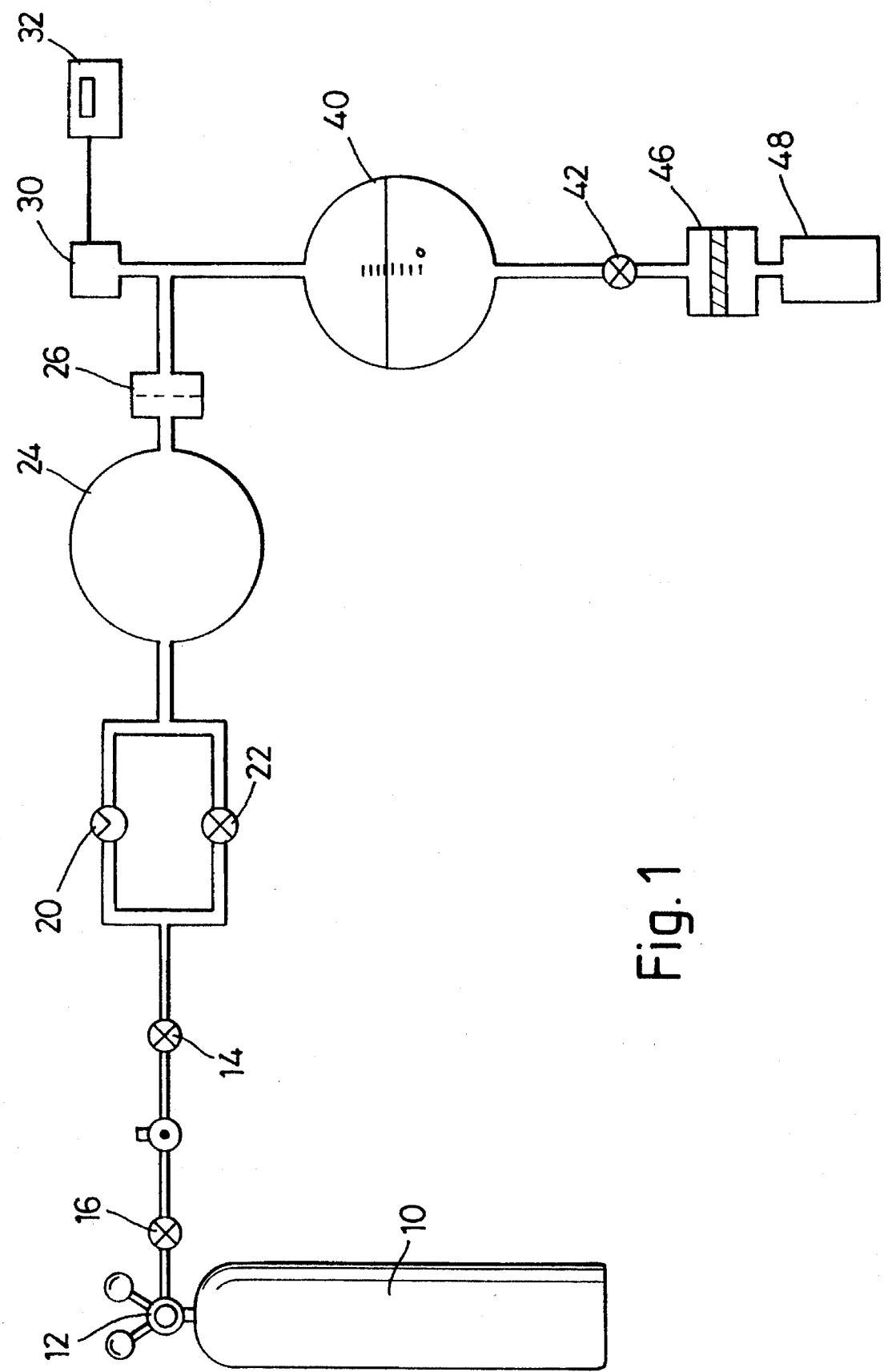
FIG. 1 is a schematic representation of the apparatus used in the Examples for the in vitro testing of antiperspirant efficacy of compositions in accordance with the invention.

Water and certain organic substances can interact to form different structures of liquid crystal. An example of this teaching is to be found in "Biological Membranes" by D. Chapman, Academic Press New York, 1968, Chapter 3, the content of which is incorporated herein by reference. Amongst the more defined liquid crystal structures that can be formed are cubic liquid crystal structures, which have a long-range periodicity in three dimensions, and hexagonal structures, which have a long-range periodicity in two dimensions.

It has surprisingly been found that certain amphiphilic substances (an amphiphilic substance by definition having both hydrophilic and hydrophobic portions in its structure), or mixtures of amphiphilic substances, when used as antiperspirant actives, have an appropriate relative insolubility in water, but also pass through physical phases on the addition of water in which they form, in their final state, liquid crystal structures of greater than one dimensional periodicity, such as those mentioned above. As such, these materials form good antiperspirant actives. Preferably, the antiperspirant actives in accordance with the invention have a solubility in water (or sweat) of less than about 0.1% by weight (at 35° C.), more preferably less than about 0.05% by weight.

In addition, at certain concentrations of solution with water, these amphiphilic materials may pass through physical phases of one dimensional periodicity or less, such as a lamellar phase, or a simple liquid phase, in which they remain fairly fluid. These types of structures are thought not to be conducive to good antiperspirant activity, unless on subsequent contact with more perspiration they form a liquid crystal structure of greater than one dimensional periodicity.

However, and without wishing to be bound by theory, on the addition of more perspiration, the amphiphilic compound(s) in a composition according to the invention may pass through further physical states, and form liquid crystal structures of greater than one dimensional periodicity. These have a sufficiently rigid structure to physically block the openings of skin pores producing the perspiration, in much the same way as conventional aluminium antiperspirant astringents are thought to work, and hence prevent perspiration.

Preferred amphiphilic materials in accordance with the invention are those which in the environment of a perspiring axilla form the most rigid liquid crystal structures (e.g. those with three-dimensional periodicity) so as to provide the most effective, physically strongest blocking of eccrine ducts.

According to a preferred embodiment of the invention, the amphiphilic antiperspirant active is one which physically swells as it forms the liquid crystal structure on contact with perspiration, hence enhancing the pore-blocking effect. It is thought that the more the amphiphilic material swells on contact with perspiration, the more effective is the antiperspirant action that it provides.

Conveniently, the structure of the antiperspirant active can be determined by standard X-ray scattering techniques, such as those described in the "Biological Membranes" reference referred to above, and which will indicate the periodicity of any structure.

Preferred antiperspirant actives according to the invention comprise those which form the most physically rigid liquid crystal at an ambient axilla temperature, typically 30°–40° C.

Compositions according to the invention are, in preferred embodiments, free or substantially free of antiperspirant or deodorant levels of metal salts. Regarding antiperspirant metal salts, these are typically aluminium and/or zirconium salts, often present in prior art antiperspirant compositions at a concentration of around 10% by weight or more. Additionally, aluminium salts are known to have deodorant activity at a concentration of around 5% by weight or more. For further guidance regarding antiperspirant metal salts, a non-limiting list of antiperspirant metal salts is provided by the FDA in "Antiperspirant drug products for over the counter human use, a tentative final monograph", Fed. Register 47:36592 (1982).

A preferred category of amphiphilic materials which form effective antiperspirant actives according to the invention comprises lipid substances, in particular lipids, which may for example be found to occur naturally in the human skin. Some examples of lipids which form effective antiperspirant actives according to the invention are glyceryl monooleate, optionally as a mixture with oleic acid, and a mixture of glyceryl monolaurate and oleic acid. When the antiperspirant active according to the invention comprises a mixture of glyceryl monolaurate and oleic acid, preferably the ratio of glyceryl monolaurate to oleic acid is from 3:2 to 4:1. Further examples of preferred lipid materials which form effective antiperspirant actives according to the invention include glyceryl monolaurate in combination with any of oleyl alcohol, isostearyl alcohol or a mixture of isostearyl alcohol and stearyl alcohol. Mixtures of polyoxyethylene ethers are also suitable actives according to the invention.

Other amphiphilic substances which form effective antiperspirant actives according to the invention include surfactants, such as, for example, a mixture of sodium oleate with oleic acid or oleic alcohol, or potassium oleate with oleic acid or oleic alcohol.

Another category of amphiphilic substances which form effective antiperspirant actives according to the invention are emulsifiers, such as, for example, a mixture of lecithin and oleic acid or oleic alcohol.

A further category of antiperspirant actives according to the invention are polymer amphiphilic complexes, such as for example, a mixture of Merquat 100 (poly(dimethyl diallyl ammonium chloride)), and sodium dodecyl sulphate (SDS), in a equimolar mixture of Merquat 100 monomer: SDS. The resulting mixture is capable of forming a hexagonal liquid crystal structure on contact with water.

Yet another category of antiperspirant actives according to the invention are block copolymer surfactants, for example sodium 10-$\Omega$-butyl [poly (dimethysiloxy) dimethyl silyl] decanoate.

Where the antiperspirant active according to the invention comprises a mixture containing more than one amphiphilic substance, it is preferable that, of the amphiphilic substances in the mixture, at least one of these substances has a more strongly hydrophobic portion (i.e. has a relatively low HLB value), whilst at least one of the substances has a more strongly hydrophilic portion (i.e. has a relatively high HLB value).

Antiperspirant compositions according to the invention which contain as their antiperspirant active amphiphilic materials, particularly lipids and especially lipids which occur in the human skin, and preferably (but not exclusively) are free or substantially free of antiperspirant or deodorant levels of metal salts, have several advantages over conventional, essentially metal-based antiperspirant compositions. First, it is possible for these materials, once applied, either to be washed away from the skin, or to be gradually metabolised by the skin, thereby to unblock the skin pore. Antiperspirant actives according to the invention may therefore be perceived by the public as relative healthy and/or mild. This is in contrast to conventional antiperspirant materials, such as aluminium, which in practice are retained by the skin in the vicinity of the skin pore having hydrolysed to insoluble substances, and are only removed once the skin cells around the pore die and are shed by the body.

Certain antiperspirant actives according to the invention, such as glyceryl monooleate, can be absorbed by the skin, and in the process of doing so they absorb water which is drawn into the skin, thereby producing a moisturising effect. Additionally, materials such as glyceryl monooleate are substantially cheaper than certain conventional antiperspirant astringents, such as activated aluminium chlorohydrate (AACH).

Compositions according to the invention also have other advantages over conventional antiperspirant compositions.

For example, certain antiperspirant actives according to the invention, such as glyceryl monolaurate, are known antimicrobial agents, thereby imparting an important additional property to the composition. Compositions according to the invention may readily have a natural pH balance on the skin, and are thereby less likely to cause skin irritation. They also have a reduced tendency to cause permanent staining to clothing.

Many antiperspirant materials according to the invention have been found to be compatible with conventional (e.g. aluminium) antiperspirant materials, and can thus be used in mixtures with aluminium- or zirconium-based antiperspirant materials to form antiperspirant compositions. It is preferred (but not mandatory) however, that such conventional metal salt actives are not used in combination with the antiperspirant actives of the invention, as this tends to negate the advantages to be had from the invention as compared with the prior art.

The antiperspirant actives according to the invention may comprise from about 5 to about 100%, more preferably from about 10 to about 80%, even more preferably from about 15 to about 60%, by weight of the antiperspirant composition.

Other Ingredients

The antiperspirant composition according to the invention may comprise other ingredients, depending on the nature and form of the finished product. Such additional ingredients should not however interfere with the ability of the antiperspirant active to form, in the residual composition on the skin, the required water-insoluble liquid crystal phase of greater than one-dimensional periodicity.

Examples of other ingredients which can optionally be present in a composition according to the invention include:

- cosmetically acceptable vehicles, such as straight-chain and branched alcohols, for example ethanol, isopropanol, or isobutanol;
- volatile and non-volatile silicones, such as dimethyl cyclosiloxanes, such as DOW CORNING fluids DC 344 and DC 345, or polydimethylsiloxane, having a viscosity in excess of 5 mm$^2$ s$^{-1}$, for example from 50 to 100 mm$^2$ s$^{-1}$, such as DOW CORNING 200 Fluids (standard viscosities 50–1000 mm$^2$ s$^{-1}$);
- deodorants, possibly including deodorant levels of metal salts,
- deoperfumes, and deodorant compounds which can also act as antimicrobial agents, such as unsaturated fatty acids, or other antimicrobial agents, e.g. Irgasan DP300, ex Ciba Geigy;
- hydrophobic oils, such as liquid paraffin oils;
- inorganic electrolytes, such as sodium chloride and sodium sulphate
- cationic polymers, such as Abil Quat 3272 and Abil Quat 3270, both ex.TH Goldschmidt AG;
- thickeners, such as clays, for example Bentone 38 (trade mark), silicas, for example Aerosil 200 (trade mark), and hydroxypropyl celluloses such as Klucel (trade mark) and other cellulose derivatives conventionally used for thickening purposes;
- skin feel improvers, such as talc and finely divided polyethylene, an example of which is Acumist B18;
- gelling agents, such as stearyl alcohol or waxes, for example castor wax;
- humectants, such as polyols, for example glycerol;
- emollients;
- sunscreens;
- perfumes;
- preservatives and antioxidants;
- skin benefit agents, such as allantoin;
- colours;
- other cosmetic adjuncts conventionally employed in stick, roll-on lotion, liquid spray, cream, and propellant-driven aerosol antiperspirant products.

The ingredients other than the antiperspirant active can conventionally form the balance of the composition, and accordingly may form up to about 95% by weight of the total composition, preferably from about 20 to about 90%, even more preferably from about 40 to about 85%, by weight of the total composition.

Product Form

The composition according to the invention can take the form of liquid or solid products, each of which is suited to, or adapted for, topical application to human skin. One convenient form of the composition according to the invention is a solid stick, usually contained in a suitable holder or dispenser to enable it to be applied to the area of the skin, particularly the underarm, where control of perspiration and deodorancy is required.

Another form of the composition of the invention is a lotion suitable for inclusion in a roll-on dispenser, fitted with a ball valve, to enable the product to be rolled on to the skin in a manner which is conventional in the art. A further example of a composition according to the invention is a liquid composition for dispensing via a finger-operated pump spray or a hand-operated squeeze spray to provide for delivery to the skin of a finely divided spray or aerosol, without the use of propellant gases to deliver it.

Alternatively, a composition according to the invention can take the form of a liquid, containing suspended particulate solids, which is suited to, or adapted for, topical application to human skin from an aerosol container. The aerosol container can then be used to dispense the composition as a spray to enable it to be applied to the area of the skin, particularly the underarm, where control of perspiration and deodorancy is required.

The composition according to the invention can also take the form of a cream, suited to, or adapted for, topical application to the human skin, e.g. by massaging or rubbing in with the fingers.

Use of the Composition

The invention provides for the use of an antiperspirant composition in accordance with the invention in perspiration control, following topical application to the human skin.

A particularly preferred composition according to the invention is an antiperspirant composition containing an antiperspirant active according to the invention, and a hydrophobic clay, especially a Bentone (trade mark) clay, most especially Bentone 38. It has been found that formulations containing Bentone clays have superior properties to similar compositions not containing Bentone in terms of improved efficacy. The Bentone clay may be present in the formulation at a concentration of from about 5–20%, more preferably from about 8–15% by weight of the total composition.

A further preferred composition according to the invention is one which comprises a surfactant which strongly interacts with the skin, thereby causing improved adhesion of the antiperspirant active to the skin. Such suitable surfactants include, for example, cationic surfactants, alpha-hydroxy acids, alkyl lactylates and other surfactants having head groups which have a relatively strong affinity for the skin surface. Preferably, such additives may be present in the composition at a concentration of from about 0.1 to 2% by weight of the total composition.

EXAMPLES

Examples 1 to 8 below are examples of two-component antiperspirant actives according to the present invention which form, upon contact with sweat, reverse cubic liquid crystal structures (having 3-dimensional periodicity):

|  | % w/w |
| --- | --- |
| Example 1 | |
| Oleyl alcohol | 24–26 |
| Glyceryl monolaurate | 76–74 |
| Example 2 | |
| Oleyl alcohol | 5–13 |
| Triethylene glycol mono hexadecyl ether | 95–87 |
| Example 3 | |
| Ceramides (from bovine brain) | 5–30 |
| Glyceryl monooleate | 95–70 |
| Example 4 | |
| Oleyl alcohol | 70–75 |

|  | % w/w |
|---|---|
| Hexadecyltrimethylammonium chloride | 30–25 |
| Example 5 | |
| Cyclohexane | 23.5 |
| Didodecyldimethylammonium chloride | 76.5 |
| Example 6 | |
| Lysozyme | 20 |
| Glyceryl monooleate | 80 |
| Example 7 | |
| Diethylene glycol mono oleyl ether | 66–76 |
| Pentaethylene glycol mono oleyl ether | 34–24 |
| Example 8 | |
| Isostearyl alcohol | 21–26 |
| Glyceryl monolaurate | 79–74 |

Examples 1, 2, 3, 7 and 8 are particularly preferred antiperspirant actives in accordance with the invention.

Examples 9 to 21 below are examples of two-component antiperspirant actives according to the invention which form, upon contact with sweat, reverse hexagonal liquid crystal phases (having 2-dimensional periodicity):

|  | % w/w |
|---|---|
| Example 9 | |
| Olyel alcohol | 28–44 |
| Glyceryl monolaurate | 72–56 |
| Example 10 | |
| Oleyl alcohol | 15–25 |
| Triethylene glycol mono hexadecyl ether | 85–75 |
| Example 11 | |
| Dodecyltrimethylammonium chloride | 29 |
| Oleic acid | 71 |
| Example 12 | |
| Oleyl alcohol | 40 |
| Distearyldimethylammonium chloride | 60 |
| Example 13 | |
| Oleic acid | 40 |
| Distearyldiemthylammonium chloride | 60 |
| Example 14 | |
| Oleic acid | 34–50 |
| Lecithin | 66–50 |
| Example 15 | |
| Glyceryl monooleate | 90 |
| Tetradecane | 10 |
| Example 16 | |
| Glyceryl monooleate | 95–65 |
| Hexadecane | 5–35 |
| Example 17 | |
| Diethylene glycol mono oleyl ether | 80 |
| Pentaethylene glycol mono oleyl ether | 20 |
| Example 18 | |
| Glyceryl monooleate | 87–80 |
| Silicone oil (DC 246 ex Dow Corning) | 13–20 |
| Example 19 | |
| Oleic acid | 50–60 |
| Alkyl polyglucoside (APG 600 ex Henkel) | 50–40 |
| Example 20 | |
| Oleyl alcohol | 50–60 |
| Alkyl polyglucoside (APG 600 ex Henkel) | 50–40 |

|  | % w/w |
|---|---|
| Example 21 | |
| Isostearyl alcohol | 30–45 |
| Glyceryl monolaurate | 70–55 |
| Example 22 | |
| Glyceryl monooleate | 95 |
| Batyl alcohol | 5 |
| Example 23 | |
| Glyceryl monooleate | 95 |
| Chimyl alcohol | 5 |
| Example 24 | |
| Glyceryl monooleate | 95 |
| 1-mono-isostearyl glyceryl ether | 5 |

Examples 9, 10, 18, 20 and 21 are particularly preferred antiperspirant actives in accordance with the invention.

The following example 25 of a single-component antiperspirant active according to the invention forms, upon contact with sweat, a "gel" liquid crystal-type phase which is a repeating bilayer structure in which the lipid chains are ordered (i.e. has a greater than one-dimensional periodicity):

| Example 25 | % w/w |
|---|---|
| Triethylene glycol mono hexadecyl ether | 100 |

The invention will now be further described by way of example only. The following compositions were prepared, using standard techniques known in the art. For the formulations not containing Bentone, it was sufficient simply to mix together the components of the mixture, and make the composition to the appropriate amount with a solvent such as ethanol. However, for the formulations containing Bentone, it was necessary to shear the Bentone into an aliquot of the ethanol, at a high rate of shear (e.g. at approximately 75% of the maximum speed of an "Ultraturrax" mixer) for at least 5 minutes at a temperature of at least 45 degrees centigrade, before cooling the mixture and adding the remainder of the components of the composition.

|  | Composition (% w/w) | | | |
|---|---|---|---|---|
| Component | 1 | 2 | 3 | 4 |
| Glyceryl monooleate | 50 | 25 | 25 | 25 |
| Bentone 38 | — | — | — | 10 |
| DSAC* | — | 0.1 | 1.0 | — |
| Perfume | 1 | 1 | 1 | 1 |
| Thickener (Klucel M) | 0.7 | 0.7 | 0.7 | 0.7 |
| Ethanol | to 100 | to 100 | to 100 | to 100 |

*DSAC is dimethyl distearyl ammonium chloride.

In Vivo Test Procedure

Each of the compositions was tested in a standard hot-room assessment procedure. In this, human volunteers are subjected to thermal stress and gravimetric determination of the perspiration produced under the thermal stress, and this is summarised as follows:

Subjects: Panels of around 35 women who use no antiperspirants for the 14 days before the test.

Hot room: Temperatures 40° C.±2° C.; relative humidity 40%±5%.

Test Design: Subjects attended daily for 3 consecutive days. They received one treatment with the products on each of the three days. After product application on the third day, the panellist was subjected to a hot-room sitting in which sweat was collected.

Products: When testing two products, one being designated the test product and the other the control, the panel is divided into two equal groups. One group receives the test treatment on the left axilla and the control treatment on the right, while the second group receives them the other way round. Alternatively, when comparing two test products against each other and against a control product, the products are randomly applied to the axillae of the panel subjects, with the proviso that the product applied to left axilla is different from that applied to the right axilla of each subject.

Product Application: The operator conducting the test applies the test product in a standard manner, so as to deposit an appropriate quantity of product on each axilla. For a stick or roll-on product this will be on average about 300 mg of product to each axilla, whereas for an aerosol product approximately 1–1.5 grams of product is dispensed.

Sweat Collection: Absorbent cotton pads having a minimal protective gauze (to prevent transfer of the test product to the cotton pad) are used to collect the sweat. On entering the hot room, each panellist is subjected to a 40-minute 'warm-up' period, during which no sweat is collected. After this, the composition is applied for the third time, and sweat is then collected for a 20-minute period and the sweat weight determined.

Analysis of Data: The statistical treatment includes an analysis of variance which allows for side effects due to the product and the panellist. The efficacy is calculated from the geometric mean weight of sweat collected from the axillae treated with each product using the formula:

$$\% \text{ sweat reduction} = 100 \times \frac{(C - T)}{C}$$

where C is the geometric mean sweat weight from the axillae treated with the control product and T is the geometric mean sweat weight from the axillae treated with the test product where a correction has been made for the side effect.

Significance is calculated by applying Student's t-test to the logarithmically transformed weights.

Results

| Composition | % sweat reduction |
|---|---|
| 1 | 19 |
| 2 | 20 |
| 3 | 23 |
| 4 | 25 |

Additionally, no adverse effects (in terms of skin irritation) were reported by any of the subject panellists using compositions 1–4.

In Vitro Test Procedure

Compositions according to the invention were also subjected to an in vitro test method to investigate their efficacy as antiperspirant actives. The following describes the apparatus and test protocol used. The apparatus and test protocol are based on the apparatus and method described by H. H. Reller & W. L. Luedders, "Pharmacologic and toxicological effects of topically applied agents on the eccrine sweat glands", Mod. Toxicol. 4: 1–54 (1977).

Apparatus Design

The apparatus used to approximate the degree of pore blocking that would be provided by antiperspirant compositions on the skin surface is shown schematically in FIG. 1. The apparatus comprises four major elements, namely:

(a) the pressure control unit (10–32),
(b) the sweat reservoir (40),
(c) the cell (46) and
(d) the detection and measurement system (48).

(a) Pressure Control Unit

A white spot nitrogen cylinder (10) and gas regulator (12) are connected to an on/off isolation valve (14) and pressure release safety valve (16). Stainless tubing and Swagelock couplings are used for subsequent connections. The primary pressure source is followed by a parallel arrangement of needle (20) and on/off (22) valves, a gas ballast reservoir (24) and a 0.5 micron particle filter (26). The unit is terminated via a 0 to 3 Bar pressure transducer (30), with accompanying three and a half digit meter (32).

The pressure unit delvers a controlled pressure, which may be stepped or ramped as a function of time. In these experiments, which were to evaluate flow rates, the stepped mode of the apparatus was used.

The in-line particle filter (26) eliminates contamination of the sweat reservoir.

(b) "Sweat" Reservoir (40)

This is a laboratory-grade glass reservoir of one liter capacity. Connection to the preceding pressure unit is via a glass to metal seal and Swagelock coupling. Connection to the subsequent cell (46) is via a rapid action on/off valve (42) and Tygon tubing, terminated in the male portion of a Luer-Lok fitting. The reservoir (40) is easily removed for cleaning. For experiments evaluating flow rates with lipid test substances, the "sweat" may be distilled water. However, when this test method is used to evaluate ionic antiperspirant actives, the "sweat" should be a 0.2–0.3% saline solution.

Both the pressure control and reservoir units are enclosed in an aluminium box, for safety reasons. Normal operation involves a maximum pressure of less than one atmosphere above ambient.

(c) Cell (46)

a 5 μm Millipore SM filter was held in a stainless steel Millipore holder with a Luer-Lok fitting. This particular filter has a simple well-defined structure, and is appropriate for the materials tested.

(d) Detection System (48)

Liquid was collected in a measuring cylinder in the flow studies, with the rate of fluid collection being measured.

Experimental

Millipore filters are immersed in double-distilled water, at 60° C., for several hours. Occasional agitation and several water changes ensure thorough cleaning. The container is covered to keep particulate contamination to a minimum.

The "sweat" reservoir is filled to a predetermined mark with filtered, double-distilled water and pressurised to 0.2 atmospheres above atmospheric pressure via the pressure unit.

The filter is transferred to the cell, flooded with distilled water and attached to the reservoir, ensuring that all air bubbles have been expelled. A flow experiment is commenced by opening the rapid action valve between the cell and reservoir.

The average of three ten-second collections gives the unblocked filter flow rate. The filter is then impregnated with a test solution of antiperspirant active by immersion for three minutes.

The filter is removed, gently shaken, or blotted with a solution-impregnated filter paper, and introduced into a "sweat" solution to gel the entrapped test solution.

The average of three further flow experiments gives the blocked filter flow rate.

The fractional increase in filter blockage equals the fractional flow rate reduction (FFRR), where FFRR=1–Blocked flow rate (Ifb)/Unblocked flow rate (Ifu), for a constant pressure drop (PD) across the filter.

However, it is the total applied pressure (P) that is fixed in the present experiments and allowance must be made for the pressure drop in the apparatus preceding the cell; this pressure drop varies with flow rate.

The corrected formula is

FFRR=1–(Pfu/Pfb).(Ifb/Ifu)

where Pfb is the pressure drop in the apparatus preceding the filter with the filter blocked;

Pfu is the pressure drop in the apparatus preceding the filter with the filter unblocked;

Ifb is the flow rate through the blocked filter; and

Ifu is the flow rate through the unblocked filter.

The portion of the calculation which contains Pfu and Pfb represents a correction factor for the pressure drop which occurs in the apparatus before the filter, which is dependent on flow rate.

Figure 2:
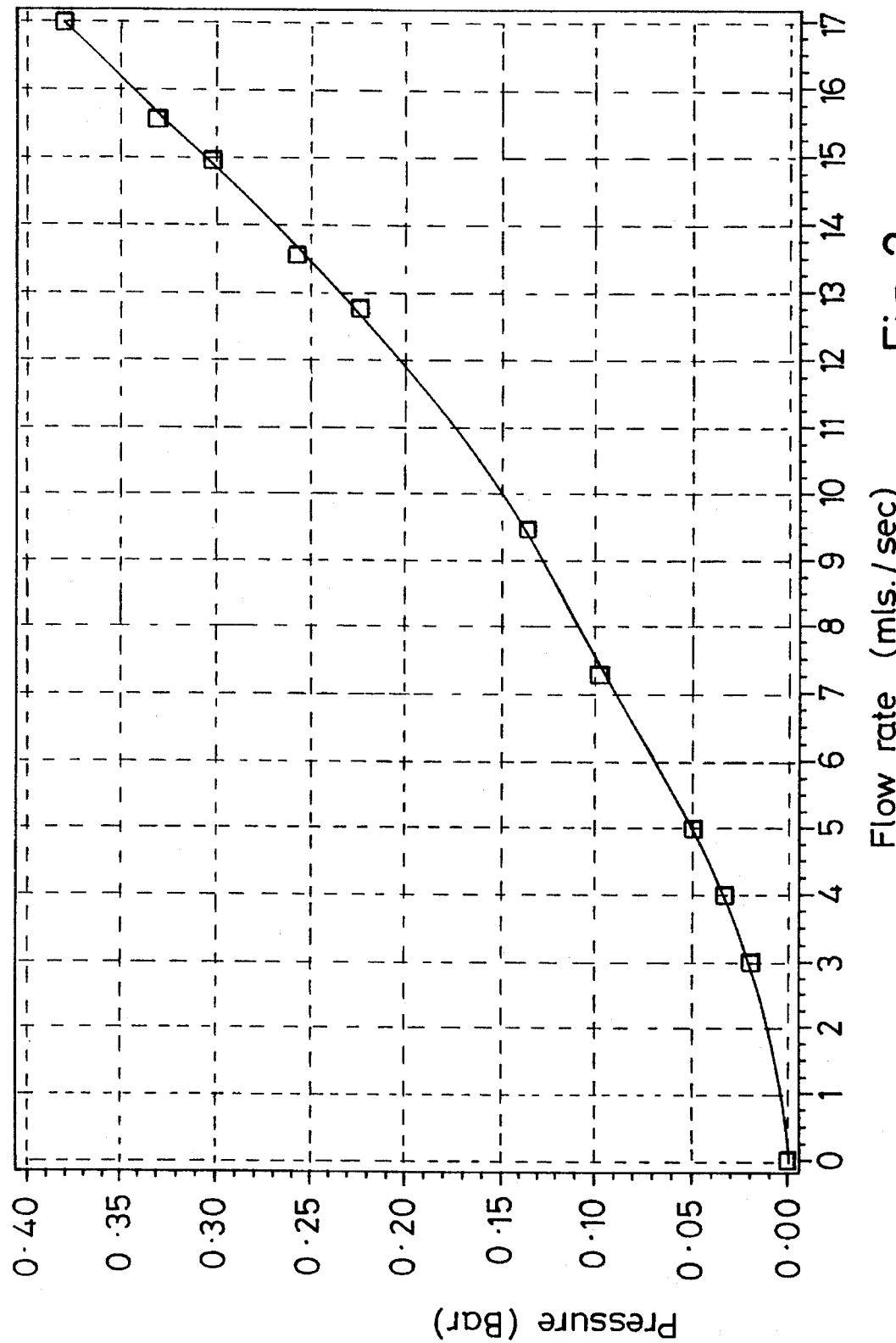
FIG. 2 is a plot of the apparatus flow rate as a function of applied pressure, with the cell detached, which may be used for determining a correction factor in the calculation which is necessary as a result of a pressure drop preceding the cell being dependent on the flow rate.

FIG. 2 shows the apparatus flow rate as a function of applied pressure, with the cell detached. Pfu and Pfb are read from the curve, at the unblocked and blocked experimental flow rates, respectively.

| Test solution | Composition (% w/w) | |
|---|---|---|
| Component | 5 | 6 |
| Glyceryl monooleate | 10 | 20 |
| Ethanol | to 100 | to 100 |
| Results | | |
| Composition | Filter blockage (%) | |
| 5 | 30 | |
| 6 | 42 | |

When compositions containing 40% or more of glyceryl monooleate were used, these caused 100% blockage of the filter.

Reproducibility: +/–3%.

For comparison, the same apparatus was used to evaluate solutions of metal containing antiperspirant actives. These were aluminium chlorohydrate (ACH) propylene glycol complex, activated aluminium chlorohydrate (AACH) propylene glycol complex, and zirconium/aluminium chlorohydrate glycine complex (ZAG), at concentration levels of 0.3, 0.6, and 1.5% by weight.

| Results | Concentration | | |
|---|---|---|---|
| Active | 0.3 | 0.6 | 1.5 |
| ACH | 12 | 27 | 61 |
| AACH | 23 | 39 | 76 |
| ZAG | 37 | 55 | 86 |

Reproducibility: better than 7%

The in vitro data confirm the known order of efficacy of the various conventional metal containing antiperspirant actives.

Compositions 7 to 15

The following compositions 7 to 15 are further examples of antiperspirant compositions according to the invention.

| Component | % w/w |
|---|---|
| Composition 7 (liquid) | |
| Glyceryl monooleate | 25 |
| Rehydrol II* | 4 |
| Perfume | 1 |
| Klucel M | 0.75 |
| Ethanol | to 100 |
| Composition 8 (liquid) | |
| Glyceryl monooleate | 25 |
| Rehydrol II | 4 |
| Perfume | 1 |
| DSAC | 1 |
| Klucel M | 0.75 |
| Ethanol | to 100 |
| Composition 9 (transparent solid stick) | |
| Active[1] | 25 |
| Sodium stearate | 9 |
| Perfume | 2 |
| Irgasan DP300 | 0.1 |
| Ethanol | 53.9 |
| Water | 10 |
| Composition 10 (transparent solid stick) | |
| Active[2] | 25 |
| Sodium stearate | 9 |
| Perfume | 2 |
| Irgasan DP300 | 0.1 |
| Ethanol | 53.9 |
| Water | 10 |
| Composition 11 (white/waxy solid stick, non-irritant) | |
| Active[3] | 25 |
| Stearyl alcohol | 23 |
| Castor wax (melting point 80° C.) | 1 |
| SUPERFINO talc | 1 |
| Perfume | 2 |
| Irgasan DP300 | 0.1 |
| Silicone oil (DC 200, 244 or 245, ex Dow Corning) | 47.9 |
| Composition 12 (white/waxy solid stick, non-irritant, improved deodorancy) | |
| Active[4] | 25 |
| Zinc phenyl sulphonate | 4 |
| Stearyl alcohol | 23 |
| Castor wax | 1 |
| SUPERFINO talc | 2 |
| Perfume | 1 |
| Silicone oil (DC 200, 244 or 245, ex Dow Corning) | 44 |
| Composition 13 (aqueous cream) | |
| Active[5] | 20–25 |
| Zinc phenyl sulphonate | 4 |
| Perfume | 2 |
| Silicone oil (DC 200, 244, ex Dow Corning) | 10–15 |
| Water | to 100 |
| Composition 14 (aqueous roll-on formulation, to be shaken prior to use) | |
| Active[6] | 20–25 |
| Zinc phenyl sulphonate | 4 |
| Perfume | 1–2 |
| Silicone oil (DC 200, ex Dow Corning) | 20 |
| Water | to 100 |
| Composition 15 (liquid, volatile based) | |
| Active[7] | 25 |
| Bentone 38 | 4 |

13
-continued

| Component | % w/w |
| --- | --- |
| Perfume | 2 |
| Ethanol | 10 |
| Silicone oil (DC 200, 245 or 50:50 mixture thereof) | to 100 |

*Rehydrol II is a 75%:25% aluminum chlorohydrate:propylene glycol complex, ex. Reheis.
[1] Glyceryl monooleate
[2] Glyceryl monolaurate 9%, isostearyl alcohol 16%.
[3] Lipid or lipid/surfactant mixture
[4] As in Example 11
[5] As in Example 11
[6] As in Example 11
[7] Lipid A further aspect of the invention can be appreciated from FIGS. 3 to 5.

A feature of the compositions according to the invention is that it is possible to illustrate advantageous compositions according to the invention using phase diagrams. A phase diagram is a diagram which can be used to display the physical structure of a multicomponent mixture at a given temperature and composition. Phase diagrams may be constructed for a composition containing any number of components, and can represent all possible combinations of those components. The figure used here show phase diagrams for a three-component mixture, but phase diagrams for two, or four or more component mixtures may equally well be used to illustrate effective antiperspirant active compositions according to the invention. To accurately illustrate the antiperspirant efficacy of a given composition, the phase diagram used should take account of at least every non-volatile component of the antiperspirant composition, i.e. those components residual on the skin after the treatment.

Figure 3:
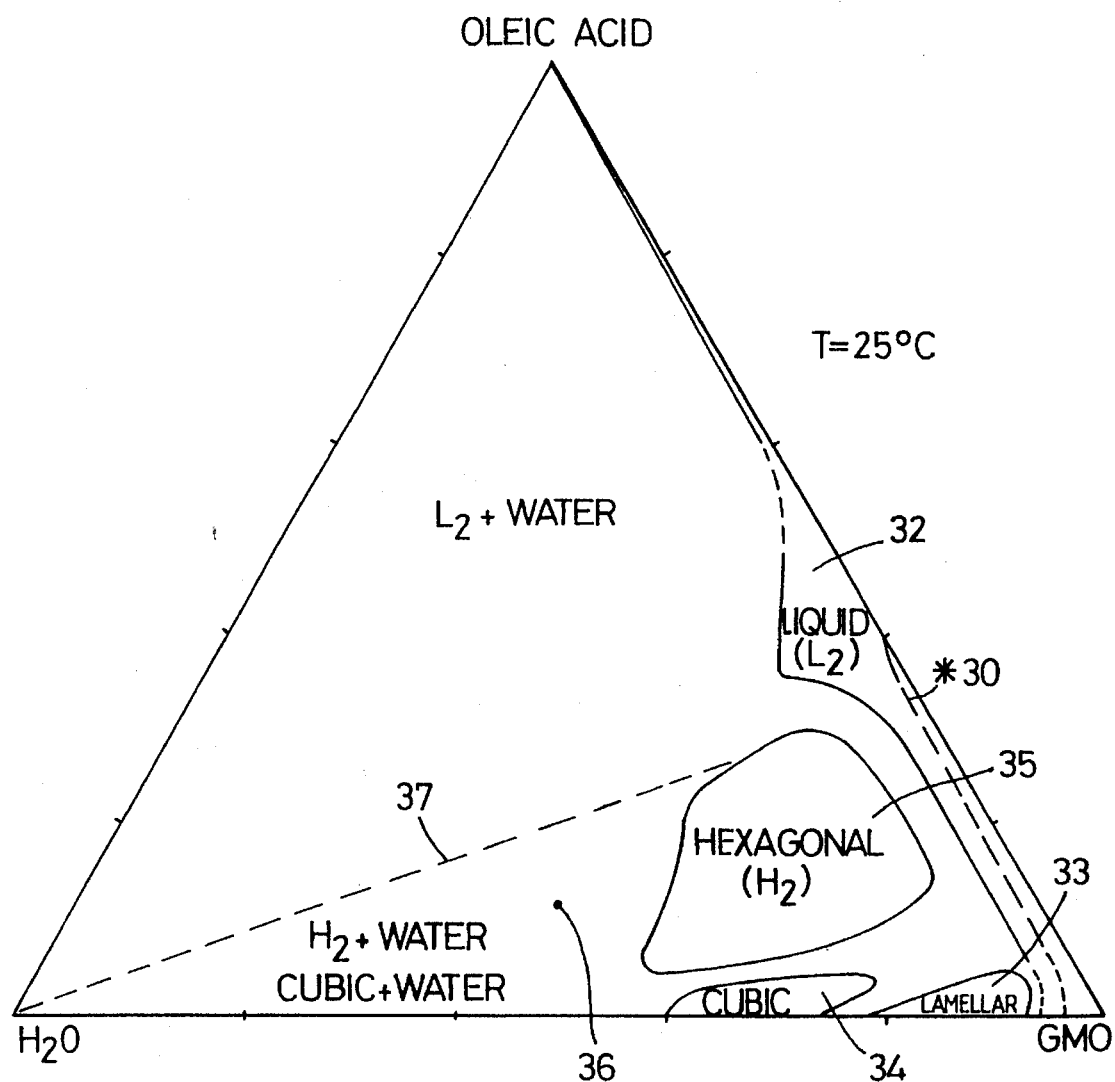
FIG. 3 is a three component phase diagram illustrating various physical phases of glyceryl monooleate/oleic acid/water mixtures which may represent (and be used for predicting) embodiments of the present invention.

FIG. 3 shows an actual triangular phase diagram for a three-component mixture of water, oleic acid and glyceryl monooleate, at 25 degrees centigrade. Shown on this diagram are some of the physical phases that are formed at various compositions represented by this diagram. These phases may be, for example, a liquid phase 32, in which the mixture has the physical structure of a free-flowing liquid. Some compositions represented also have a lamellar phase form 33, in which they have the consistency of a more viscous liquid. It has been found that these two physical phases, which do not have greater than 1 dimensional periodicity (a lamellar phase has 1 dimensional periodicity, whilst a liquid phase has zero order periodicity), do not form a very effective antiperspirant active.

However, it has been found that effective antiperspirant compositions will be those which, when applied, lie initially on this phase diagram towards the oleic acid-glyceryl monooleate (GMO) side of the diagram, preferably between the asterix 30 and the GMO corner of the diagram. In use, as the user perspires, the composition applied is exposed to more water, and in terms of the phase diagram this effectively moves the composition originally applied in a straight line towards the left of the diagram, i.e. towards the water corner. It can be appreciated from this diagram that, on doing this, the resultant composition will generally pass from the liquid 32 or lamellar 33 areas of the diagram, towards, for example, the hexagonal 35 or cubic 34 areas of the diagram. It is to be noted that, when the composition has reached a well defined physical phase, such as, for example, the hexagonal phase 35, on the further addition of water (a composition represented for example by the point 36 in FIG. 3) the observed structure of the composition is in fact a dynamic equilibrium between the hexagonal structure of liquid crystal 35 and free water. However, most of this free water is located on the eccrine gland side of the crystal structure, and thus is retained in the gland. It is when the antiperspirant composition in equilibrium with water has a greater than 1 dimensional periodicity, i.e. when it has the hexagonal 35 or cubic 34 structure, that the composition forms an effective antiperspirant active, and for this particular three-component mixture it has been generally found that compositions which lie below the dotted line 37 in FIG. 3 form effective antiperspirant active.

Figure 4:
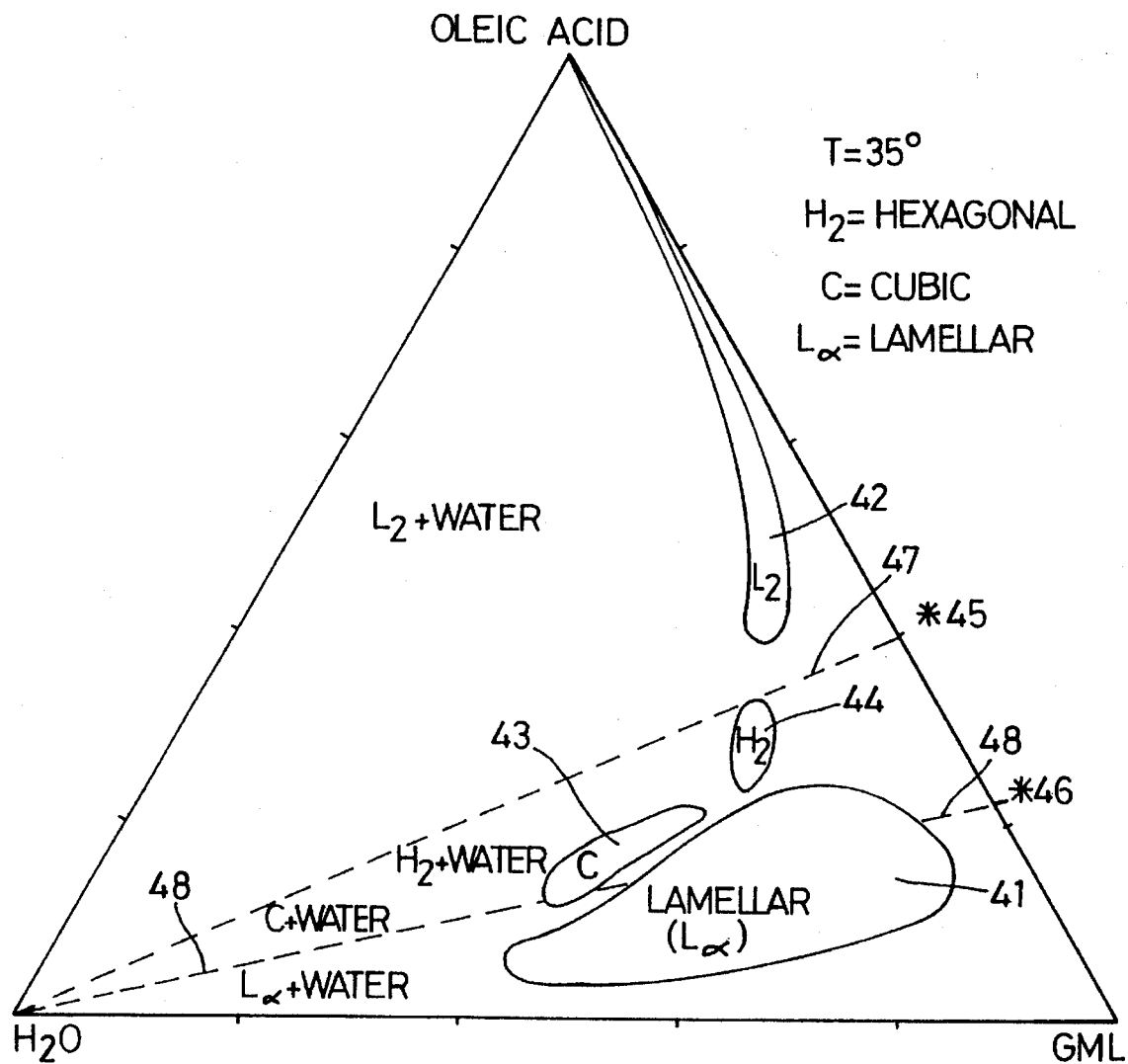
FIG. 4 is another three component phase diagram, similar to that of FIG. 3, but showing the various phases of mixtures of glyceryl monolaurate/oleic acid/water.

FIG. 4 shows a similar triangular phase diagram for a three-component mixture comprising water, oleic acid and glyceryl monolaurate (GML), at 35 degrees centigrade. Again, from this diagram it can be seen that various compositions of the three components may have different structures, such as lamellar 41, an oily liquid micro-emulsion (L2) 42, cubic 43, and hexagonal 44. It has, however, been found that antiperspirant compositions which, when applied, lie generally in the region of the diagram between the two asterixes 45 and 46, and corresponding dotted lines 47 and 48, have proved to be effective antiperspirant compositions.

Figure 5:
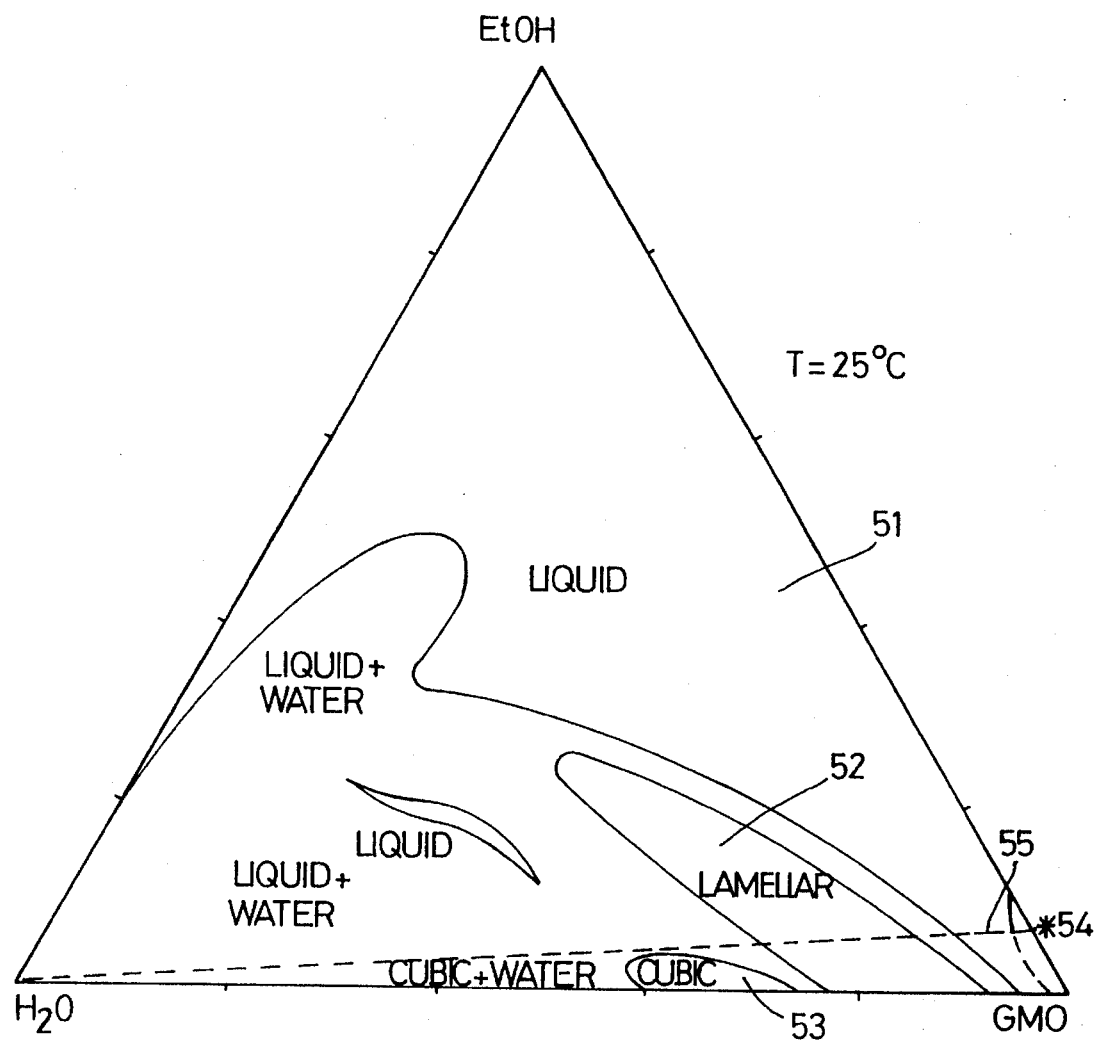
FIG. 5 is another three component phase diagram, similar to those of FIGS. 3 and 4, but showing the various physical phases of mixtures of glyceryl monooleate/ethanol/water.

FIG. 5 shows a triangular phase diagram for a three component mixture comprising water, ethanol and glycerol monooleate. The ethanol is an important component to consider, since it is a commonly used vehicle by which antiperspirant compositions are delivered. Once again, the compositions may have at least one physical form which has one dimensional order or less, such as, for example, liquid 51 or lamellar 52 phases, but also other phases 53 (having a cubic structure), which have greater than 1 dimensional order. It has been found that antiperspirant compositions which, after application and evaporative loss of ethanol, lie generally below asterix 54 and corresponding dotted line 55 in FIG. 5 form effective antiperspirant actives.

A conclusion which can be drawn from this particular diagram is that, if the antiperspirant active in the composition is solely glyceryl monooleate and the delivery vehicle comprises ethanol, the glyceryl monooleate will not be capable of forming an effective active until most of the ethanol has evaporated. Thereafter, however, GMO on its own will provide an effective antiperspirant composition.

It is thus demonstrated how phase diagrams may provide a useful indication of which compositions involving an amphiphilic substance will prove to be effective antiperspirant compositions in accordance with the present invention.

We claim:

1. An antiperspirant composition suitable for topical application to human skin comprising an antiperspirant active which comprises an amphiphilic material in an amount of from 5 to 100% by weight of the composition, the amphiphilic material having a solubility in water at 35° C. of less than about 0.1% by weight and being one which forms, at a temperature in the range of 30°–40° C., upon contact with perspiration, water-insoluble liquid crystal structures selected from the group consisting of liquid crystal structures which have three-dimensional periodicity, liquid crystal structures which have two-dimensional periodicity, and mixtures thereof.

2. An antiperspirant composition according to claim 1, wherein the liquid crystal phase has a hexagonal structure.

3. An antiperspirant composition according to claim 1, wherein the liquid crystal phase has a cubic structure.

4. An antiperspirant composition according to claim 1 wherein the antiperspirant active swells as it forms the liquid crystal structure on contact with perspiration.

5. A method of preventing or reducing perspiration at the human skin surface, the method comprising applying thereto an antiperspirant composition suitable for topical application to human skin comprising an antiperspirant active which comprises an amphiphilic material in an amount of from 5 to 100% by weight of the composition, the amphiphilic material having a solubility in water at 35° C. of less than about 0.1% by weight and being one which forms, at a temperature in the range of 30°–40° C., upon contact with water, water-insoluble liquid crystal structures selected from the group consisting of liquid crystal structures which have three-dimensional periodicity, liquid crystal structures which have two-dimensional periodicity, and mixtures thereof.

* * * * *